United States Patent [19]
Wu et al.

[11] Patent Number: 5,886,171
[45] Date of Patent: Mar. 23, 1999

[54] 3-HYDROXY GAMMA-LACTONE BASED ENANTIOSELECTIVE SYNTHESIS OF AZETIDINONES

[75] Inventors: Guang-Zhong Wu, Somerville; Xing Chen, Plainsboro; Yee-Shing Wong, Florham Park; Doris P. Schumacher, Bedminster; Martin Steinman, Livingston, all of N.J.

[73] Assignee: Schering Corporation, Kenilworth, N.J.

[21] Appl. No.: 864,529

[22] Filed: May 28, 1997

Related U.S. Application Data

[60] Provisional application No. 60/018,752 May 31, 1996.
[51] Int. Cl.[6] .................................................. C07D 205/08
[52] U.S. Cl. ............................................................ 540/200
[58] Field of Search ................................................ 540/200

[56] References Cited

U.S. PATENT DOCUMENTS

| | | | |
|---|---|---|---|
| 5,292,939 | 3/1994 | Hollingsworth | 562/515 |
| 5,739,321 | 4/1998 | Wu | 540/200 |

FOREIGN PATENT DOCUMENTS

| | | |
|---|---|---|
| 95/08532 | 3/1995 | WIPO . |
| 97/16424 | 5/1997 | WIPO . |

OTHER PUBLICATIONS

O'Leary, J. Chem Research (S) 368, Aug. 1996.
Panfil et al, *Tetrahedron*, vol. 47, No. 48 (1991), pp. 10087–10094.
Panfil et al, *Chemical Abstracts*, vol. 109, 38139j. (1987).

*Primary Examiner*—Mark L Berch
*Attorney, Agent, or Firm*—Anita W. Magatti

[57] ABSTRACT

The invention relates to a process for producing a compound of the formula

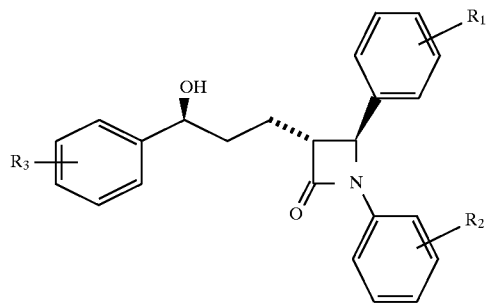

wherein $R_1$, $R_2$ and $R_3$ are as defined in the specification, which comprises the steps of: (a) reacting a lactone with an imine to obtain a chiral diol of the formula IV; (b) oxidizing the diol to obtain an aldehyde of formula V; (c) condensing the aldehyde with an enolether followed by dehydration to obtain a compound of formula VI; (d) hydrogenating the compound of formula VI to obtain a ketone of formula VII; and (e) chirally catalytically reducing the ketone, wherein steps (b)–(d) are shown in the following reaction scheme:

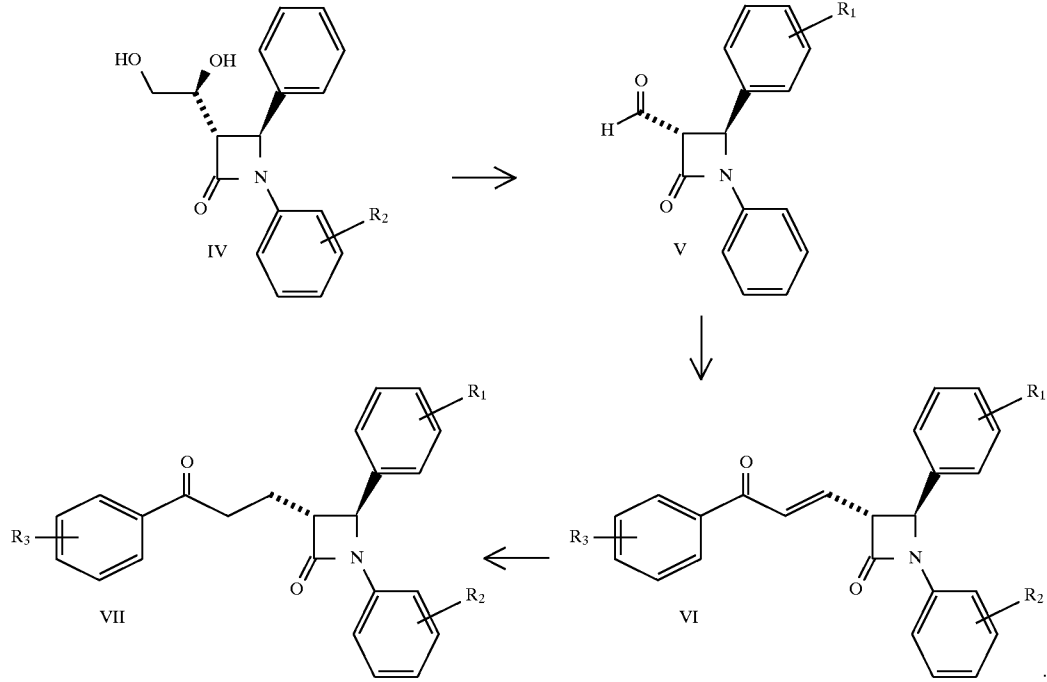

13 Claims, No Drawings

3-HYDROXY GAMMA-LACTONE BASED ENANTIOSELECTIVE SYNTHESIS OF AZETIDINONES

This application claims the benefit of U.S. Provisional Application Ser. No. 60/018,752, filed May 31, 1996.

BACKGROUND OF THE INVENTION

This invention provides an improved process for producing azetidinones useful as hypocholesterolemic agents, as disclosed in co-owned, copending PCT Publication WO 95/08532, which is equivalent to U.S. Pat. No. 5,767,115, filed Mar. 18, 1996, the disclosure of which is hereby incorporated by reference. More particularly, this invention provides the steps of producing an azetidinone represented by the formula 1.

SUMMARY OF THE INVENTION

This invention provides a process for producing a compound of the formula:

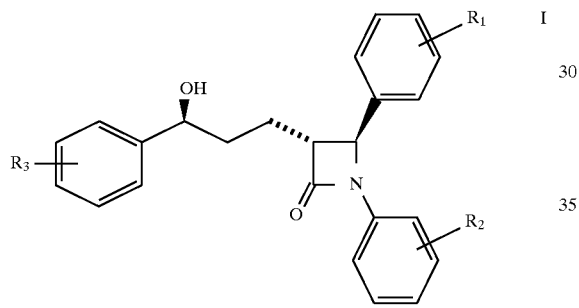

wherein:

$R_1$, $R_2$ and $R_3$ are independently selected from the group consisting of:
(a) H;
(b) halo;
(c) —$OR_5$, wherein: $R_5$ is selected from the group consisting of H, $C_1$ to $C_6$ alkyl, aryl, aralkyl, heteroaryl, $C_2$ to $C_6$ alkynyl, $C_3$ to $C_7$ cycloalkyl, $C_3$ to $C_7$ cycloalkenyl and —$C(O)R_6$; $R_6$ is selected from the group consisting of $C_1$ to $C_6$ alkyl, aryl and —$OR_7$; and $R_7$ is $C_1$ to $C_6$ alkyl or aryl; and
(d) —$C(O)R_8$, wherein: $R_8$ is selected from the group consisting of $C_1$ to $C_6$ alkyl, aryl, heteroaryl, aralkyl, cycloalkyl, —$OR_9$ and —$N(R_{10})_2$; $R_9$ is selected from the group consisting of $C_1$ to $C_6$ alkyl and aryl; and each $R_{10}$ is independently selected from the group consisting of H, $C_1$ to $C_6$ alkyl and aryl.

In particular, this process is useful for preparing 1-(4-fluorophenyl)-3(R)-[3(S)-hydroxy-3-(4-fluorophenyl)propyl]-4(S)-(4-fluorophenyl)-2-azetidinone.

In general, this process comprises reaction of a γ'-lactone and an imine to form a β-lactam, followed by a chiral reduction. In particular, this invention is directed to a process for preparing a compound of formula I

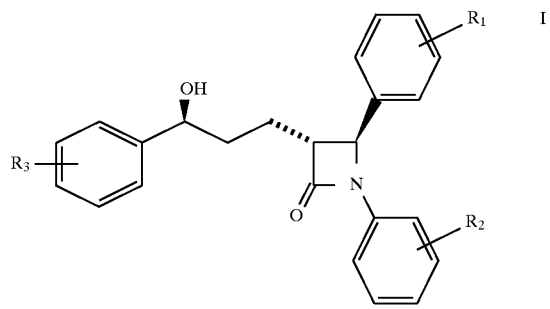

wherein $R_1$, $R_2$ and $R_3$ are as defined above, comprising
(a) reacting lactone of formula II

with an imine of formula III

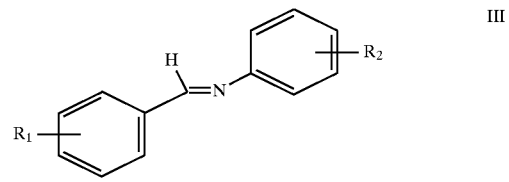

in the presence of a base, and optionally in the presence of a cyclization promoter, to obtain a chiral diol of formula IV

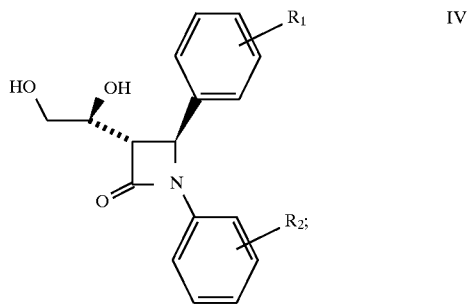

(b) oxidizing the chiral diol of formula IV to the corresponding aldehyde of formula V

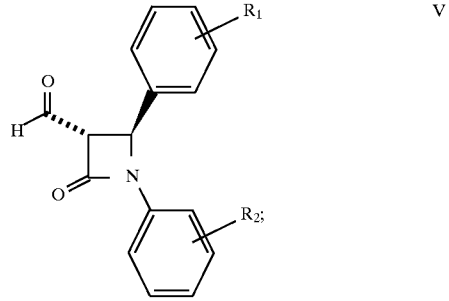

(c) condensing the aldehyde of formula V with an enolether of the formula E

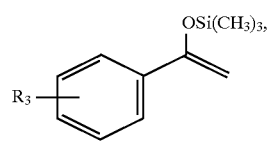

followed by dehydration to obtain a compound of formula VI

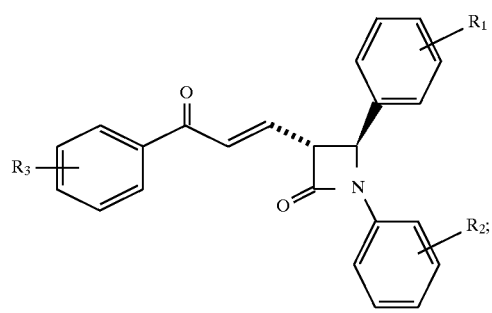

(d) hydrogenating a compound of formula VI to form a compound of formula VII

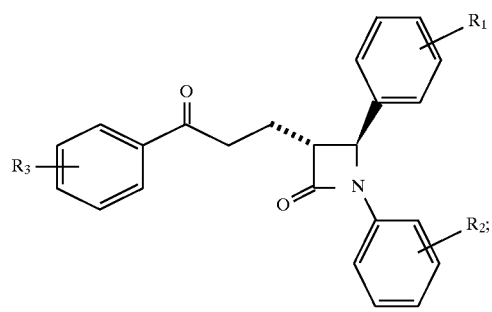

(e) conducting a chiral catalytic reduction of the compound of formula VII and a chiral catalyst to obtain a compound of formula (f) optionally, when any of $R_1$, $R_2$ or $R_3$ is a benzyloxy or alkoxy group, converting said benzyloxy or alkoxy group to a hydroxy group to obtain a compound of formula I.

Also claimed are the following processes for preparing intermediates:

The process of reacting a lactone of formula II with an imine of formula III in the presence of a base and optionally in the presence of a cyclization promoter to obtain a chiral diol of formula IV.

The process of oxidizing a chiral diol of formula IV to obtain an aldehyde of formula V.

The process of condensing an aldehyde of formula V with an enolether of formula E, followed by dehydration to obtain a compound of formula VI.

The process of hydrogenating a compound of formula VI to obtain a ketone of formula VII.

The process of hydrogentating a compound of formula VI"

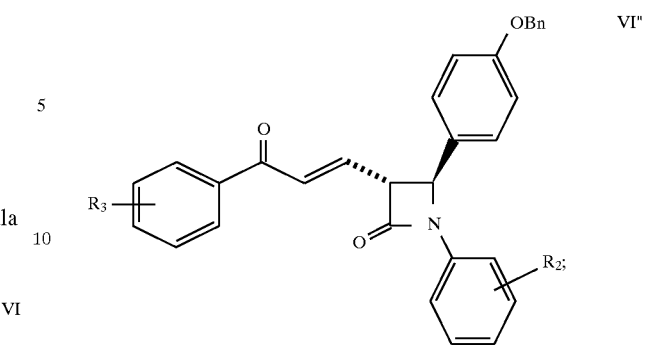

to obtain a compound of formula X

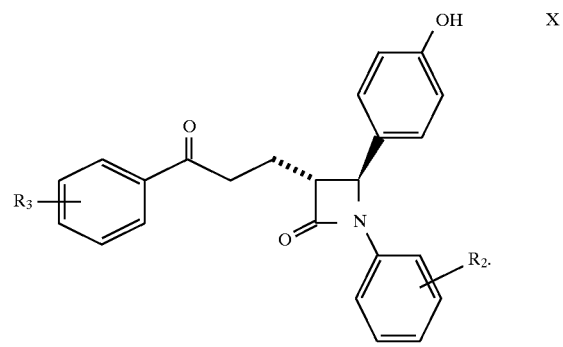

The process of chirally reducing the keto group in the compound of formula VI" to obtain a compound of formula XI

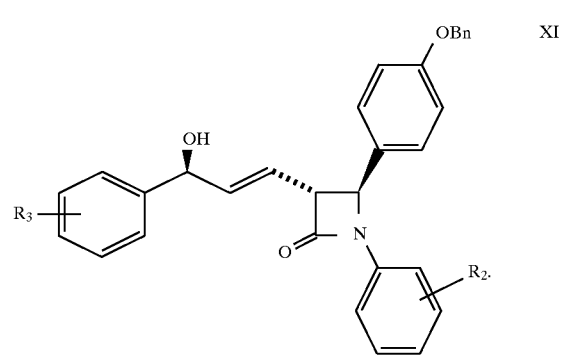

Also claimed are the intermediates of formulas IV and VI.

DETAILED DESCRIPTION

As used herein the term "lower alkyl" means straight or branched alkyl chains of 1 to 6 carbon atoms. Alternatively, the number of carbon atoms may be specified. Thus, "$C_1$ to $C_6$ alkyl" means straight or branched alkyl chains of 1 to 6 carbon atoms. "Lower alkoxy" refers to alkoxy groups having 1 to 6 carbon atoms. Alternatively, the number of carbon atoms may be specified. Thus, "$C_1$ to $C_6$ alkoxy" means straight or branched alkoxy chains of 1 to 6 carbon atoms.

"Alkenyl" means straight or branched carbon chains having one or more double bonds in the chain, conjugated or unconjugated, and alkadienyl refers to chains having two double bonds in the chain. Alternatively, the number of carbon atoms may be specified. Thus, "$C_1$ to $C_6$ alkenyl" means straight or branched alkenyl chains of 1 to 6 carbon atoms. "Alkynyl" means straight or branched carbon chains having one or more triple bonds in the chain. Alternatively, the number of carbon atoms may be specified. Thus, "$C_1$ to $C_6$ alkynyl" means straight or branched alkynyl chains of 1 to 6 carbon atoms.

Where an alkyl, alkenyl or alkynyl chain joins two other variables and is therefore bivalent, the terms alkylene, alkenylene and alkynylene are used.

"Aryl" (including substituted aryl) means a carbocyclic group containing from 6 to 15 carbon atoms and having at least one aromatic ring (e.g. aryl is a phenyl ring), with all available substitutable carbon atoms of the carbocyclic group being intended as possible points of attachment, said carbocyclic group being optionally substituted by 1 to 3 substituents selected from the group consisting of halo, alkyl, hydroxy, phenoxy, $CF_3$, amino, alkylamino, dialkylamino and $-NO_2$.

"Aralkyl" means an alkyl group as defined above, in which an aryl group as defined above is substituted for one of the alkyl H atoms, e.g., benzyl, 4-nitro-benzyl' 4-methoxy benzyl and 4-chlorobenzyl.

"Acid" means an organic acid such as p-toluene sulfonic acid, trifluoroacetic acid or trifluoromethane sulfonic acid. Alternatively "acid" means an inorganic acid such as sulfuric acid, hydrochloric acid or phosphonic acid.

"Hydrogenation catalyst" means a transition metal or its salt such as Pd/C, Pt/C, Raney nickel, Rh/C, Ru/C, PdO, PtO or $(PPh_3)_3RhCI$.

"Cycloalkenyl" mean a cycloalkane of 4 to 10 carbon atoms with one or more double bonds in the ring.

"Bn" means benzyl. "BnO" means benzyloxy.

"Cycloalkyl" means a saturated carbon ring of 3 to 6 carbon atoms, while "cycloalkylene" refers to a corresponding bivalent ring, wherein the points of attachment to other groups include all positional isomers. Alternatively, the number of carbon atoms may be specified. Thus, "$C_3$ to $C_6$ cycloalkyl" means a saturated carbon ring of 3 to 6 carbon atoms.

"Halogeno" or "hal" or "halogen" refers to fluorine, chlorine, bromine or iodine radicals.

"Heteroaryl" means a 5- or 6-membered aromatic ring comprising 1 or 2 hetero atoms selected from the groups consisting of nitrogen and oxygen, for example pyridyl, pyrimidyl, imidazolyl, pyrrolyl, furanyl and oxazolyl. All positional isomers for a given heteroaryl group as defined herein are contemplated, for example 2-pyridyl, 3-pyridyl and 4-pyridyl. Heteroaryl also means benzofused heteroaryl radicals formed by the bonding of a benzene radical to adjacent carbon atoms on a heteroaryl ring as defined above; examples are indolyl, quinolyl, quinazolinyl, quinoxalinyl, indazolyl, benzoxazolyl, benzothienyl and benzofuranyl.

"Ph" means phenyl.

"Suitable inert organic solvent" means any organic solvent or combination of solvents that is unreactive in the reaction being conducted and is a solvent for the reactants. Such solvents used in the various reactions of this invention are identified in the discussion of reaction schemes and in the examples. Typical suitable solvents are halogenated compounds such as chloroform or dichloromethane; heterocyclic compounds such as tetrahydrofuran (THF); 1,3-dimethyl-3,4,5,6-tetrahydro-2(1H)-pyrimidinone (DMPU), dimethylformamide (DMF); dimethylsulfoxide (DMSO), lower alkanols ($C_1$–$C_6$ branched or straight chain alkanols) such as methanol, acetonitrile and carbocyclic aromatics such as toluene.

"Lewis acid" means an acid such as $BF_3$.etherate, $TiCl_4$ or $AlCl_3$.

In one aspect, the process of this invention comprises reaction of a γ-lactam and an imine to form a β-lactam, followed by a chiral reduction according to Reaction Scheme A just below.

Reaction Scheme A

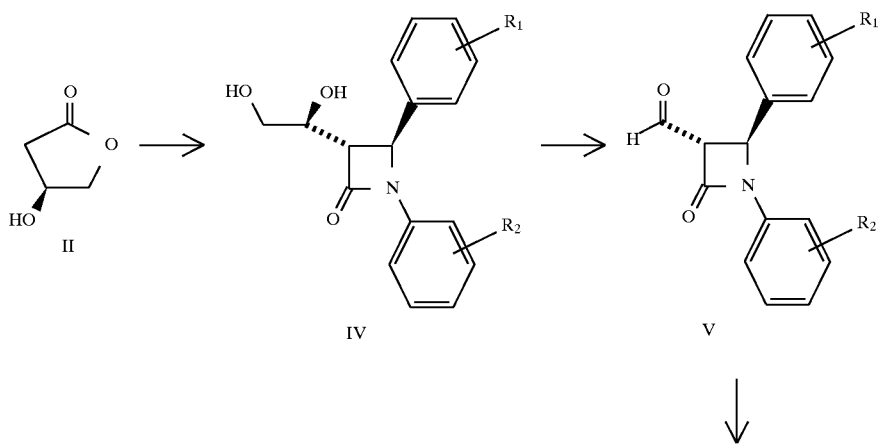

-continued
Reaction Scheme A

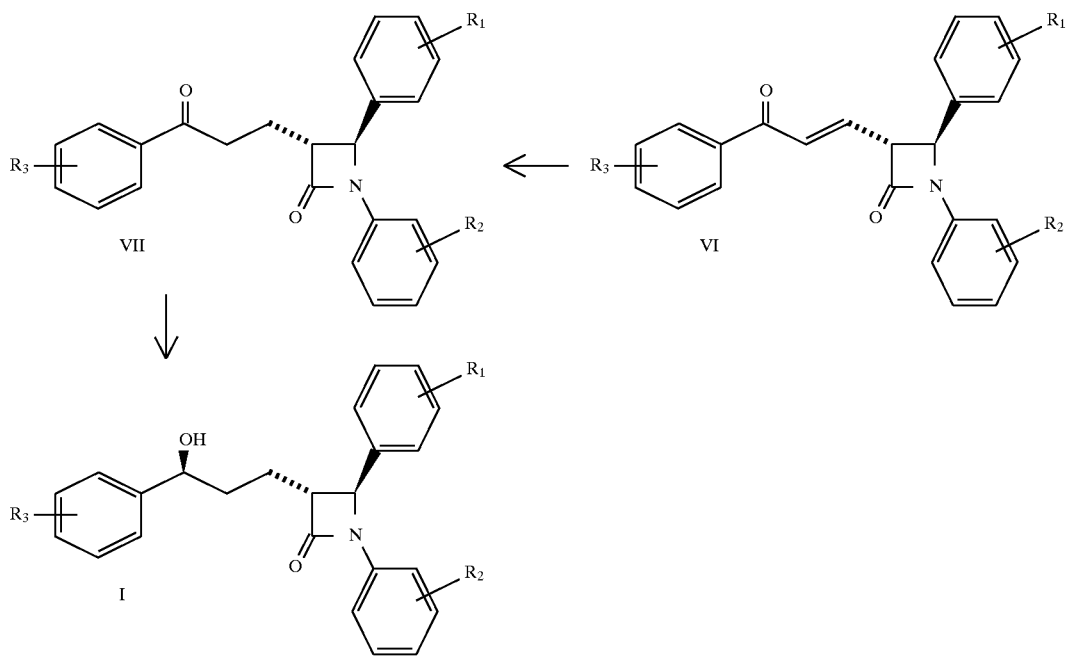

This process, designated Method A, for producing compounds of formula 1, wherein the moieties

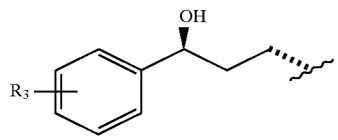

and

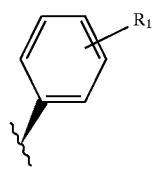

have trans relative stereochemistry, comprises the following steps:

(a) reacting lactone of formula II with an imine of formula III in the presence of a strong base and optionally in the presence of a cyclization promoter, to obtain a chiral diol of formula IV;

(b) oxidizing the resulting chiral diol of formula IV to the corresponding aldehyde of formula V, for example with an oxidizing agent such as $NaIO_4$ or $H_5IO_6$;

(c) condensing the aldehyde of formula V with an eno-lether of the formula E

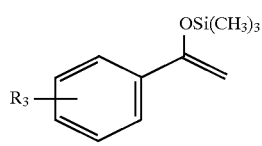

followed by dehydration, for example acid catalyzed dehydration, to obtain a compound of formula VI;

(d) hydrogenation of a compound of formula VI with a hydrogenation catalyst agent such as hydrogen over palladium or hydrogen and $(PPh_3)RhCl$ on carbon to form a compound of formula VII;

(e) conducting a chiral catalytic reduction of the compound of formula VII with a borane, such as $BH_3 \cdot (CH_3)_2S$ or borane-THF complex, and a chiral catalyst such as

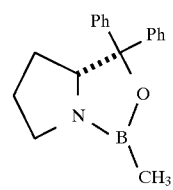

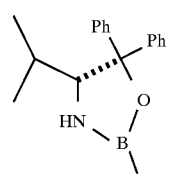

or

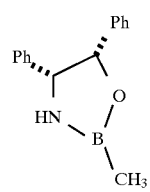

to obtain a compound of formula I;

(f) optionally, when any of $R_1$, $R_2$ or $R_3$ is a benzyloxy or alkoxy group, converting said benzyloxy or alkoxy group to a hydroxy group, for example conducting a debenzylation reaction with a hydrogenating agent such as Pd/C/NH₃HCO₂H or converting an alkoxy group to a hydroxy group by treatment with a Lewis acid to obtain a compound of formula I.

Method A is described in more detail is as follows. In step (a) of Reaction Scheme A, the lactone II is treated in a strong base such as lithium diisopropylamide (LDA) with an imine of formula III under a dry atmosphere at a temperature in the range of about −15° to about −35° C. in a suitable inert organic solvent, e.g., DMPU, to produce a β-lactam of formula IV. The reaction can be quenched by an acid such as acetic acid, and a trans β-lactam of formula IV can be recovered by extraction followed by crystallization. Because trans β-lactam cyclizes faster than cis β-lactam, formation of a trans isomer is favored. This cyclization can be greatly accelerated by addition of additives such as LiCl or LiBr (in a solvent such as DMF) resulting in further selectivity of trans β-lactam formation. A crystallization step at this stage further improves the ratio of trans to cis β-lactam to 95:5. In this reaction, use of a weaker coordination metal favors the formation of a trans β-lactam of formula IV. Thus, in this reaction, the use of sodium lithium hexamethyldisilyl amide (LIHMDA) as a base favors the formation of a trans β-lactam of formula IV as opposed to the cis isomer, and is preferred as opposed to Et₂Zn/LDA or LiN(Pr-i)₂. Also in this reaction, a lower temperature favors the formation of a trans β-lactam of formula IV, as opposed to the cis isomer; and thus −35° C., is preferred over −25° C. or −15° C.

In step (b), a β-lactam of formula IV is oxidized by treatment with an oxidizing agent such as NaIO₄ in a mixture of solvents such as THF and water at a temperature between about 10° C. and 25° C., with about 10° C. to about 15° C. being preferred. The ratio of the oxidizing agent, NaIO₄, to diol is as follows: if the diol is present at 1.0 equivalent, then the NaIO₄ is present at 1.0–2.0 equivalents, with 1.5 equivalent being preferred. The organic solvent for the reaction is a polar aprotic solvent such as acetonitrile or THF. The reaction is quenched by adding the reaction mixture to ice water. The resulting aldehyde of formula V is extracted and concentrated for use in the next step of the process.

In step (c), an aldehyde of formula V is reacted with the enolether of the formula E in an aprotic anhydrous organic solvent such as toluene in the presence of a Lewis acid such as BF₃.etherate at a temperature in the range of about −78° C. to about −20° C., with about −40° C. to about −20° C. being preferred. The resulting aldol reaction can be quenched, for example with a mixture of NaHCO₃, t-BuOMe and hydrogen peroxide. In this reaction, the ratio of the β-lactam and the enolether can be as follows: if the β-lactam is present at 1.0 equivalent, then the enolether can be present at 0.9 to 1.2 equivalent with 1.0 equivalent being most preferred. The ratio of the β-lactam and BF₃.etherate can be as follows: if the β-lactam is present at 1.0 equivalents, then BF₃.etherate can be present at 1.0 to 1.5 equivalent, with 1.0 to 1.2 equivalent being preferred.

The resulting solution containing aldol product is extracted and concentrated for the dehydration step which involves treatment with molecular sieves and an organic acid such as p-toluene sulfonic acid monohydrate. If the aldol product is present at 1.0 equivalent, then the p-toluene sulfonic acid monohydrate can be present at 0.4 to 0.8 equivalent, with 0.5 to 0.6 equivalent being preferred. The solvents which may be employed in this reaction include toluene, t-butyl methyl ether (t-BuOMe), or benzene. The molecular sieves which are used in this reaction are 3A or 4A and are present in the reaction at 100% to 200% weight/weight as compared to the aldol compound. The reaction temperature is about 35° C. to about 100° C., with the range of about 45° C to about 60° C. being preferred. The resulting compound of formula VI is filtered and concentrated for use in the next step of this process. It will be appreciated that a compound of formula VI is formed with cis and trans stereochemistry. That is,

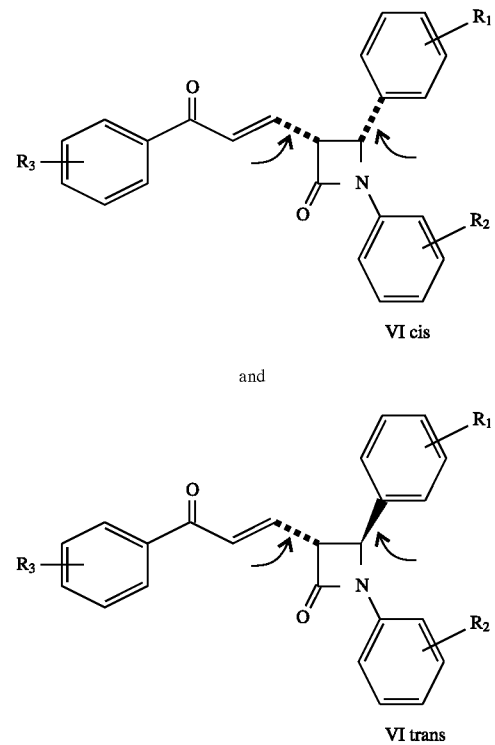

VI cis and

VI trans cis and trans about the azetidinone ring as shown by the arrows in these diagrams. Obtaining the compound with the trans stereochemistry is necessary in order to get the desired final products of the invention.

In step (d), the compound of formula VI is hydrogenated by treatment with a hydrogenating agent such as (Ph₃P)₃RhCl/H₂ under a hydrogen atmosphere in an organic solvent such as a mixture of ethyl acetate (EtOAc) and CH₃OH; CH₂Cl₂; toluene; or benzene. The ratio of hydrogenating agent to the compound of formula VI is as follows: if the compound of formula VI is present at 1 mol %, then the hydrogenating agent is present at 0.1 to 10 mol %, with 0.3 mol % being preferred. The hydrogen atmosphere is present at 5 to 100 psi, with 40 to 60 psi being preferred. The reaction is run for 10 to 30 hours, with 14 to 16 hours being preferred. After extraction and concentration, the resulting compound of formula VII is used in the next step.

In step (e), the compound of formula VII is chirally reduced by reaction in an anhydrous organic solvent such as CH₂Cl₂, THF or toluene, in the presence of a borane, such as BH₃.(CH₃)₂S or borane-THF complex, and a chiral reduction catalyst such as

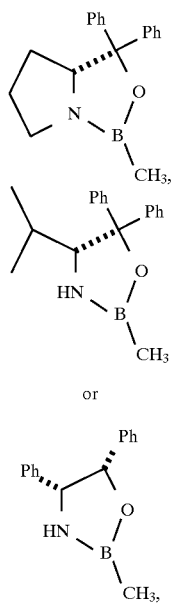

or

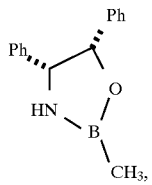

at a temperature in the range of about −30° to about 0° C., with a range of about −20° to about −10° C. being preferred. The reaction is run for about 1 to about 20 hours, with a range of about 3 to about 10 hours being preferred. The ratio of the compound of formula VII to the chiral reduction catalyst is as follows: if the compound of formula VII is present at 1.0 equivalent, then the catalyst is present in a range of about 5 mol % to 100 mol %, with 5 mol % to 10 mol % being preferred. If the compound of formula VII is present at 1.0 equivalent, then the borane (e.g., $BH_3.Me_2S$) is present at 0.7 to 1.0 equivalent, with 0.7 to 0.8 equivalent being most preferred. Concentration, extraction, and crystallization leads to the reduced compound of formula I.

For compounds of formula I wherein any one of $R_1$, $R_2$ or $R_3$ is benzyloxy or alkoxy, said compounds can be converted to other compounds of formula I wherein $R_1$, $R_2$ or $R_3$ is hydroxy by methods well known in the art. This is important in the preferred process described below, wherein the desired compound of formula I has a hydroxy group at $R_1$, but wherein the hydroxy group must be protected during the process, preferably by a benzyl group. The protected compound of formula I is debenzylated by treatment with a hydrogenating agent such as $Pd/C/HCO_2NH_4$ under a hydrogen atmosphere: the concentration of Pd/C is 5% to 20% w/w, with 10–15% w/w being preferred. The ratio of compound of formula I to Pd/C used is 1.0 equivalent of compound of formula I to 2.0 to 5.0 equivalents of Pd/C, with 3.0 to 4.0 equivalent of Pd/C being preferred. Alternatively, hydrogen gas is used in the ranges from 5 psi (pound per square inch) to 100 psi with 20 to 40 psi being preferred. The solvents which can be employed at this stage of the reaction include $CH_3OH$, ethanol and i-propanol. Alkoxy groups can be converted to hydroxy groups by well-known methods, for example by treatment with a Lewis acid. Those skilled in the art will recognize that a reactive substituent at any of $R_1$, $R_2$ or $R_3$, such as hydroxy or amino, can be protected with a suitable protecting group during the claimed process and said protecting group can be removed after the desired compound of formula I is obtained.

As noted above, when trans β-lactam is formed in step (a), the corresponding cis product is also formed. The cis product is present at this stage of the process in an amount of 5% as compared to the trans product. The cis product may now be purged out by crystallization.

In a preferred embodiment of the invention, an imine of the formula

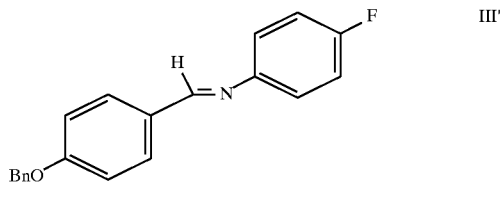

is used and an enolether of the formula E'

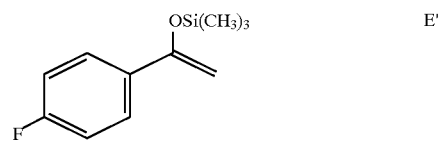

is used. Consequently the compound of formula VI which results has the structural formula VI':

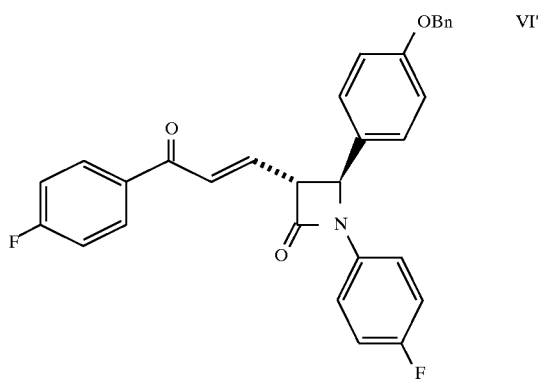

This resulting compound of formula VI' is hydrogenated as described above, the resulting in a compound of formula VII'

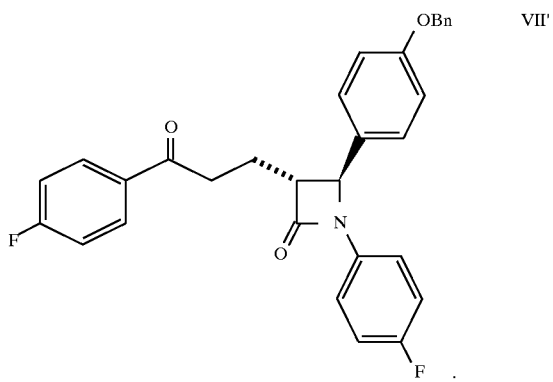

The compound of formula VII' is chirally reduced as described above, in the presence of a chiral reduction catalyst to obtain the reduced compound of formula I'

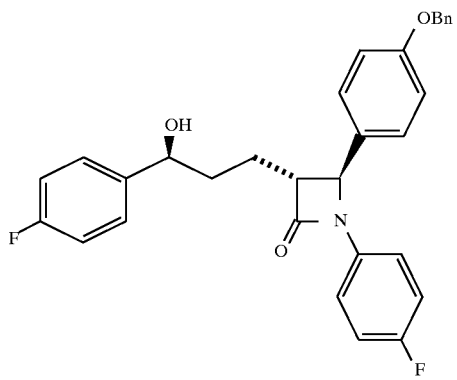

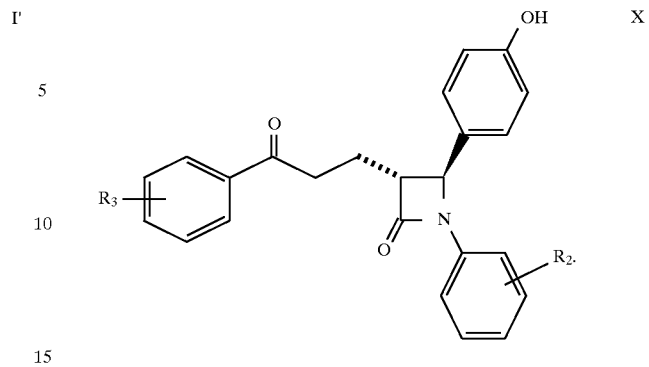

The compound of formula I' is debenzylated by treatment with a hydrogenating agent such as Pd/C/HCO$_2$NH$_4$ under a hydrogen atmosphere to obtain a compound of formula I"

The carbonyl adjacent to the R$_3$-substituted phenyl group is then chirally reduced to obtain the corresponding compound of formula I'''

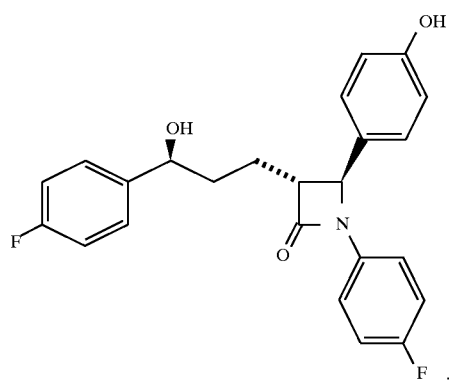

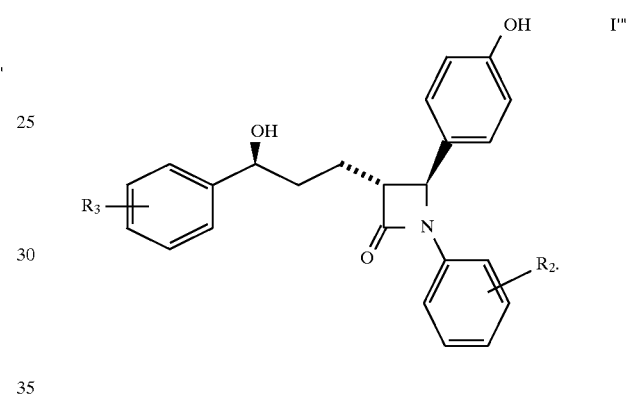

Alternatively, a compound of formula VI"

In particular, a compound of formula VI' undergoes double hydrogenation as described to obtain a compound of formula X'

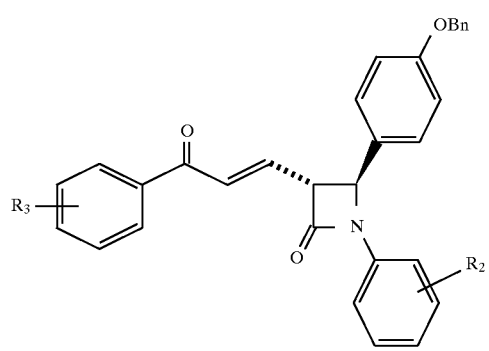

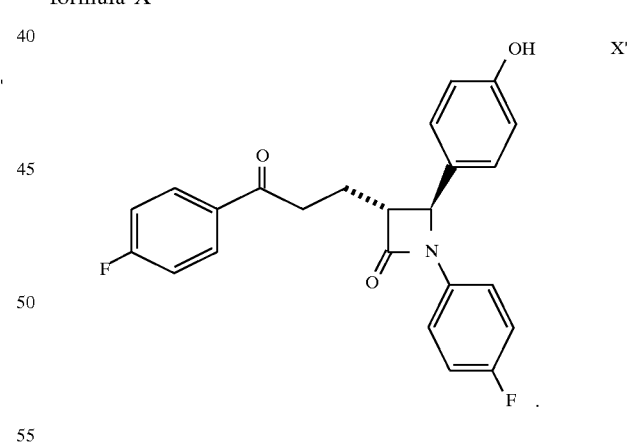

may undergo a double hydrogenation step by reaction under hydrogen in the presence of a hydrogenation catalyst such as palladium on carbon to obtain a compound of formula X Alternatively, in a process of the invention, a chiral reduction of the keto group in a compound of formula VI" may be conducted to obtain a compound of formula XI

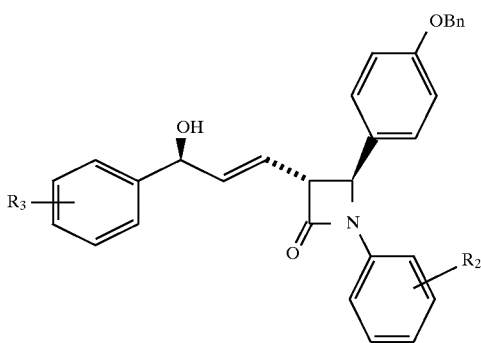

The double bond and the BnO group of this compound of formula XI may then be hydrogenated to obtain the compound of formula I'''.

In particular, the compound of formula VI' can be chirally reduced to the compound of formula XI'

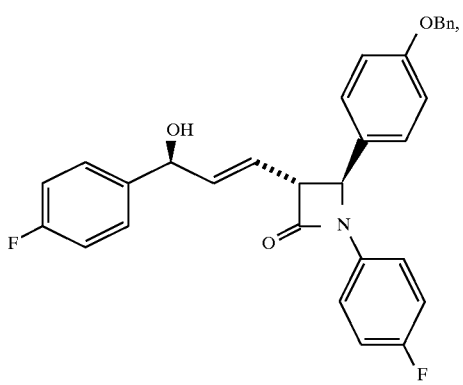

which can then be hydrogenated to obtain the compound of formula I''

In another process of the invention, a compound of formula VI'' may be converted by the Noyori reduction, i.e. using the catalyst $(R)$—Ru(BlNAP)Cl$_2]_2$.NEt$_3$, to obtain the compound of formula I'''. In particular, a compound of formula VI' can be reduced by this method to obtain a compound of formula I''.

The starting material of formula II is known, and may be prepared from s-malic acid of the formula

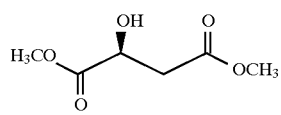

by reduction with BH$_3$Me$_2$.S followed by treatment with 5% NaBH$_4$ to obtain a compound of the formula

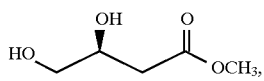

followed by cyclization of this compound with CF$_3$CO$_2$H to obtain the γ-lactone of formula II.

Alternatively, the γ-lactone of formula II may be obtained from glucose as described in U.S. Pat. No. 5,292,939, Hollingsworth, which is hereby incorporated by reference.

An imine of formula III' may be prepared by reacting 4-benzyloxy-benzaldehyde with 4-fluoroaniline in a polar organic solvent such as isopropanol at about room temperature. Other imines of the formula III may be prepared in a similar manner, by reacting the appropriate benzaldehyde derivatives and the appropriate aniline derivatives in isopropanol at room temperature for 2 to 3 hours and filtering the reaction mixture to give the product as a solid.

An enolether of the formula E' may be prepared by reacting 4-fluoro-acetophenone (which is a known compound or may be prepared by known methods) in a solution of lithium diisopropylamide in a polar organic solvent such THF at a temperature in the range of about −30° C. to about −35° C., with quenching by addition of Me$_3$SiCl, concentration and distillation to obtain the enolether product. Other enolethers of formula E may be prepared in a similar manner.

The following examples illustrate the process of this invention:

EXAMPLE 1

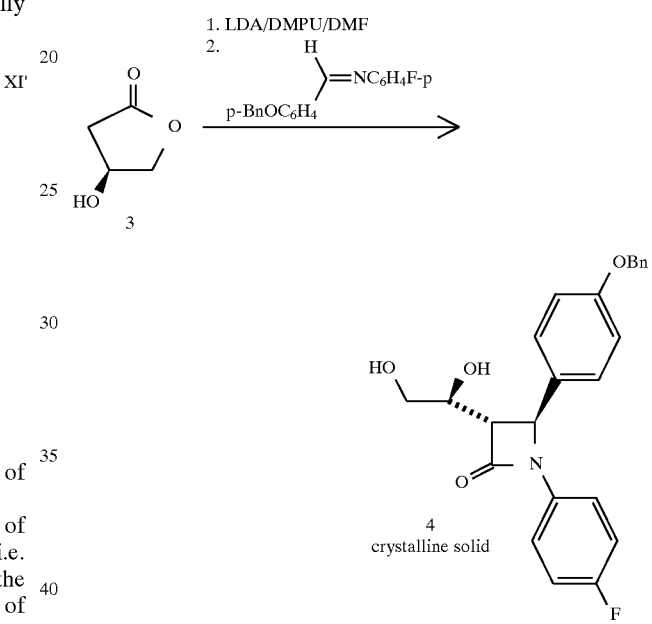

To a 5-liter 3 neck flask equipped with a mechanical stirrer, thermometer and addition funnel were added 500 mL of THF, 400 mL of DMPU and 120 mL (0.92 mol) of diisopropylamine. To the cooled mixture at −40° to −45° C. was added dropwise 368 mL (0.92 mol) of 2.5M n-BuLi hexane solution. After 20 minutes, 47 g (0.46 mol) of lactone 3 diluted in 250 mL of THF was introduced and the reaction was agitated at −40° to −45° C. for 2 hr. While agitating, 100 g (0.328 mol) of imine was dissolved in 1 liter of DMF and then was added dropwise through the addition funnel into the reaction mixture at −40° to −45° C. (30 min.). The reaction was maintained at −25° to −30° C. for 14 to 18 hrs and warmed to −13° to −17° C. for another 4 hrs as followed by HPLC. 14 g of LiCl was dissolved in 400 mL DMF in a 500 mL flask and added into the reaction mixture. After another 2 hrs at −15° C., 200 mL of HOAc was added to quench the reaction.

The reaction mixture was poured slowly into a 10-liter extractor containing 2 liters of 3N HCl, 1 liter ice and 2.5 liters of EtOAc. The mixture was stirred for 15 min. and separated into layers. The aqueous layer was extracted with 1.0 liter and then with 0.5 liter of EtOAc. The combined organic layers were washed with 4×2 liter brine, concentrated, and 250 mL toluene was added to crystallize the trans lactam 4. The solid was filtered and dried at 50° C. to give 85.5 g (64% yield) lactam 4. Mp: 119°–120° C. $^1$H NMR (CDCl$_3$) 7.38 (m, 5H), 7.22 (m, 4H), 6.90 (m, 4H), 5.04 (d, J=2.0, 1H), 5.02 (s, 2H), 4.21 (m, 1H), 3.70 (m, 1H), 3.6 (m, 1H), 3.52 (d, J=5.0, 1H), 3.15 (dd, J=5.2, 2.0 Hz), 2.85 (t, J=5.3, 1H). $^{13}$C NMR (CDCl$_3$) 165.5, 160.7, 159.0, 157.5, 136.7, 133.6, 133.5, 129.3, 128.7, 128.2, 127.6, 127.4, 118.8, 118.6, 116.0, 115.5, 70.1, 69.5, 62.9, 56.8. HRMS: 408.1619 (MH+); Calc'd: 408.1611. $[\alpha]_D^{25}$=−69.78 (c=0.121, THF). Anal.Calc'd for C$_{24}$H$_{23}$FNO$_4$: C, 70.75; H, 5.44; N, 3.44. Found: C, 70.57; H, 5.56; N, 3.41.

EXAMPLE 2

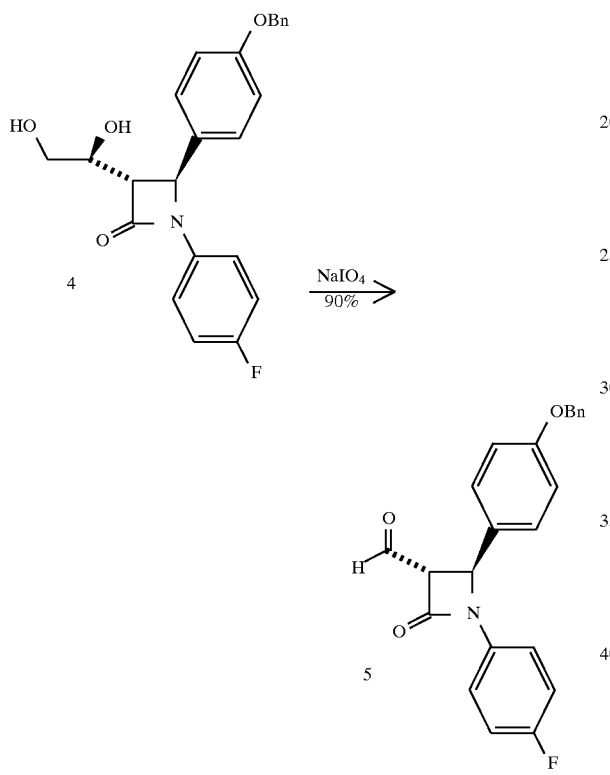

To a 2 liter 3-neck flask equipped with a mechanical stirrer, thermometer and addition funnel were added sequentially 100 g (0.246 mmol) of lactam 4 and 800 mL of CH$_3$CN. The mixture was cooled to 10° C. with an ice bath. 63 g (0.295 mmol) of NaIO$_4$ was dissolved in 800 mL of water in a 1 liter flask and transfered into the addition funnel. The NaIO$_4$ solution was added into the reaction mixture at such a rate to maintain the temperature below 20° C. (20 min.). After addition, the reaction was warmed to room temperature (r.t.) and stirred for 1 to 2 hrs as followed by NMR. The reaction was quenched into a 6 liter extractor containing 1.5 liters of ice-brine and 1.5 liters of toluene. The layers were stirred, separated and the aqueous layer was extracted with 500 mL of toluene. The combined organic layer was washed with 2×500 mL brine and concentrated to about 500 mL for the next reaction. MS: 376( MH+), 265, 239. $^1$H NMR (CDCl$_3$) 9.82 (d, J=1.3 Hz, 1H), 7.31 (m, 5H), 7.17 (m, 4H), 6.88 (m, 4H), 5.32 (d, J=2.4 HZ, 1H), 4.98 (s, 2H), 4.15 (dd, J=2.4, 1.3 Hz, 1H).

EXAMPLE 3

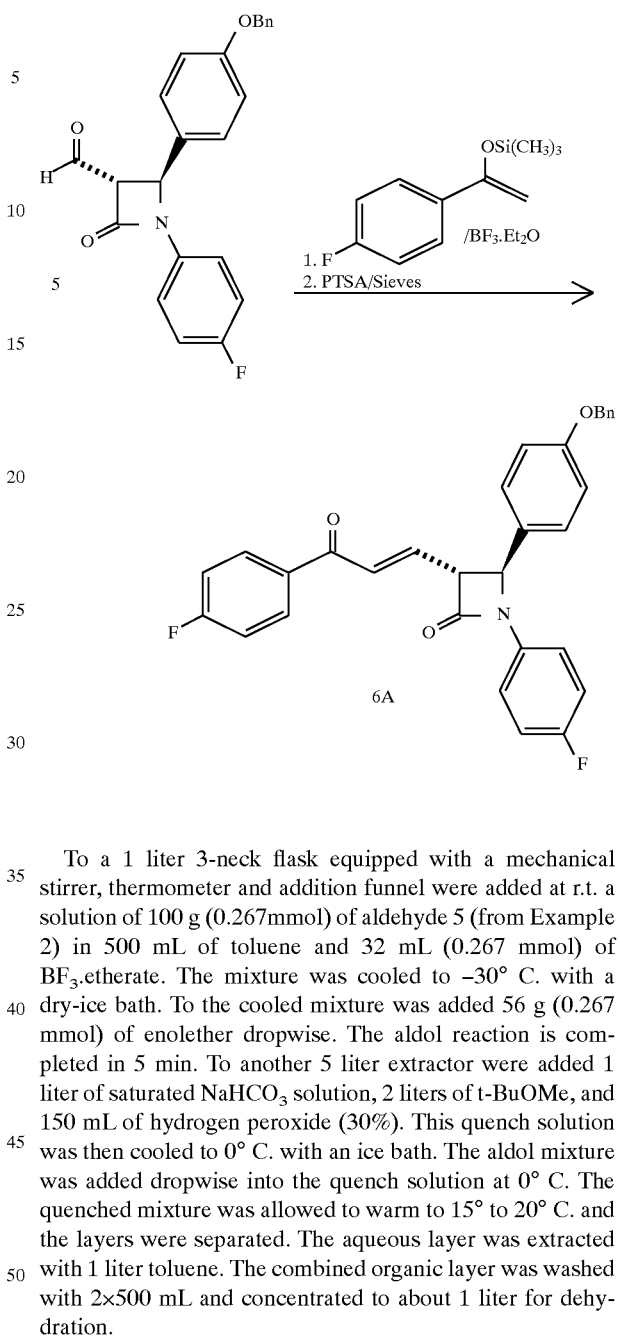

To a 1 liter 3-neck flask equipped with a mechanical stirrer, thermometer and addition funnel were added at r.t. a solution of 100 g (0.267mmol) of aldehyde 5 (from Example 2) in 500 mL of toluene and 32 mL (0.267 mmol) of BF$_3$.etherate. The mixture was cooled to −30° C. with a dry-ice bath. To the cooled mixture was added 56 g (0.267 mmol) of enolether dropwise. The aldol reaction is completed in 5 min. To another 5 liter extractor were added 1 liter of saturated NaHCO$_3$ solution, 2 liters of t-BuOMe, and 150 mL of hydrogen peroxide (30%). This quench solution was then cooled to 0° C. with an ice bath. The aldol mixture was added dropwise into the quench solution at 0° C. The quenched mixture was allowed to warm to 15° to 20° C. and the layers were separated. The aqueous layer was extracted with 1 liter toluene. The combined organic layer was washed with 2×500 mL and concentrated to about 1 liter for dehydration.

To the 1 liter toluene solution of aldol product obtained above were added 200 g of molecular sieves and 25 g (0.133 mmol) of p-toluenesulfonic acid monohydrate. This mixture was heated to 40 to 50° C. and monitored by NMR (2 to 4 hrs.). The reaction was cooled to 0° C. and filtered through a pad of MgSO$_4$ and then 100 g silica gel. The filtrate was concentrated for the next step. Alternatively, the concentrated solution was added to 400 mL of heptane to precipitate the double bond product (99 g, 7.5% overall yields). MS: 496 (MH+), 359, 305, 238. $^1$H NMR 8.01 (dd, J=8.5, 5.5 Hz, 1H), 7.40 (m, 7H), 7.30 (m, 6H), 7.18 (m, 2H), 7.22 (d, J=8.6, 1H), 6.98 (t, J=8.5 Hz, 1H), 5.08 (s, 2H), 4.88 (d, J=2.4, 1H), 4.00 (m, 1H).

EXAMPLE 4

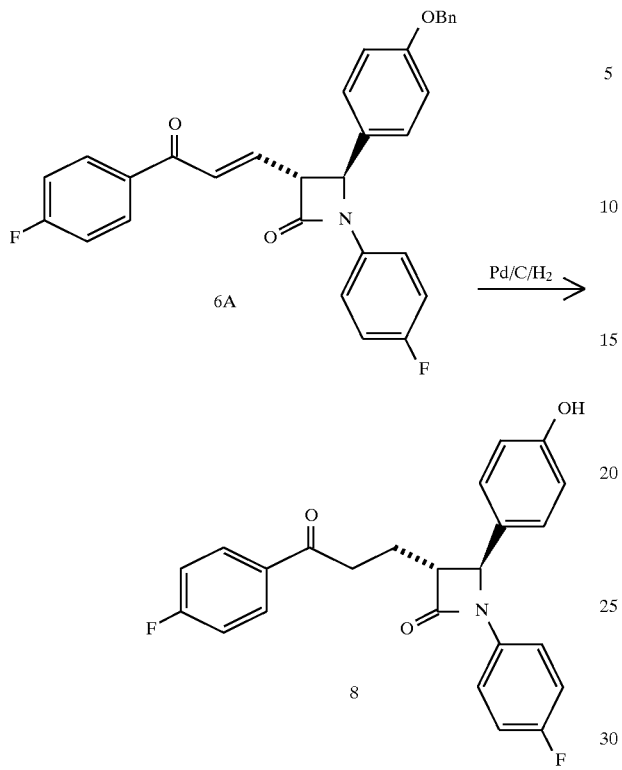

To a 1 liter Parr pressure bottle were added 0.8 g of Palladium on carbon (10%), 1.6 g (19.0 mmol) of NaHCO$_3$, 16 g (32.3 mmol) of compound 6A in 80 mL of EtOAc and 80 mL of CH$_3$OH. The bottle was shaken under 30 psi of hydrogen pressure for 2 to 3 hrs as followed by TLC and HPLC. The reaction mixture was filtered through a pad of celite and washed with 200 mL toluene. The filtrate was washed in a 1 liter extractor with 200 mL brine and 2 mL of 3N HCl. After separation of the layers, the organic layer was washed with 2×200 mL brine. Concentration gave 11.8 g (90% yield) of compound 8.

(The reaction also could be carried out as follows: A mixture of 1 g of compound 6A in 10 mL of EtOAc, 1 mL of water, and 0.5 (w/w) % of Pd/C (wet) was shaken under 25 psi of H$_2$ for ca. 4 hrs. The mixture was filtered through celite and washed with toluene. Concentration gave compound 8.

MS: 408 (MH+), 297. $^1$H NMR (CDCl$_3$) 7.95 (dd, J=8.6, 5.5 Hz, 2H), 7.13–7.22 (m, 4H), 7.09 (t, J=8.6, 2H), 6.91 (t, J=8.6, 2H), 6.80 (d, J=8.6 Hz, 2H), 4.65 (d, J=2.1, 1H), 3.26 (m, 1H), 2.33 (s, 1H), 2.25 (m, 1H). $^{13}$C (CDCl$_3$) 197.7, 167.7, 164.5, 160.7, 157.5, 156.3, 133.8, 133.0, 130.9,130.7, 129.2, 127.5, 118.6, 118.5, 116.2, 116.1, 116.0, 115.8, 115.7, 61.3, 59.7, 35.6, 23.3. Anal. Calc'd. for C$_{24}$H$_{19}$NF$_2$O$_3$.1/2 H$_2$O: C, 69.75; H, 4.47; N, 2.95; F, 9.11. Found: C, 69.23; H, 4.80; N, 3.36; F, 9.13.

EXAMPLE 5

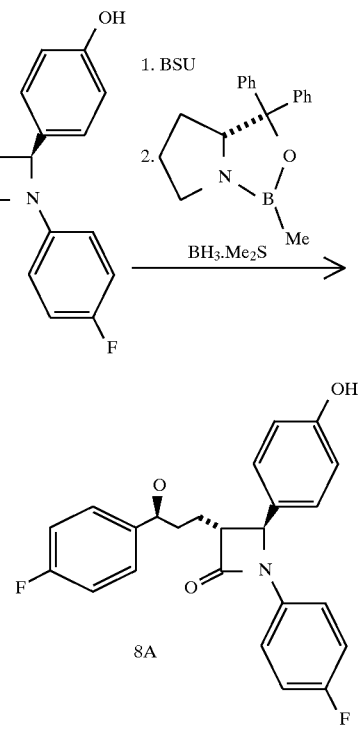

The chiral catalyst was made following the standard procedure: trimethylboroxine (28 mg, 0.22 mmol) was added into a solution of diphenylprolinol (75 mg, 0.3 mmol) in toluene (5 ml) and the resultant solution was heated until refluxing. Toluene was distilled and another 5 ml of toluene was added and distilled out. The residue was used directly in the following reaction.

To a 50 mL oven-dried flask with a magnetic stirrer were added 2.4 g (5.9 mmol) of compound 8, 10 mL CH$_2$Cl$_2$, and 0.62 g (3.0 mmol) of bistrimethylsilyl urea (BSU). After 0.5 hr, the reaction was filtered directly into another 50 mL oven-dried flask containing 0.05 eq. of the chiral catalyst at −20° C. To this was added 2.3 mL (4.7 mmol) of 2N BH$_3$.Me$_2$S. The reaction was stirred at −15° to −20° C. and monitored by TLC and HPLC (3 to 5 hrs). 10 mL methanol/HCl was added, followed by concentration. Water and t-BuOMe were added to the residue and it was extracted with t-BuOMe (×2) to give a crude product solution. Concentration of t-BuOMe lead to the recovery of >50% catalyst as the HCl salt after filtration. Crystallization of crude product from Isopropanol/H$_2$O afforded 1.9 g of compound 8A. $^1$H NMR(DMSO) 9.54 (s, 1H), 7.32 (dd, J=8.3, 5.7 Hz, 2H), 7.21 (m, 4H), 7.35 (m, 4H), 6.77 (d, J=8.3 Hz, 2H), 5.3 (d, J=4.6 Hz, 1H), 4.82 (d, J=2.1 Hz, 1H), 4.50 (m, 1H), 3.10 (m, 1H), 1,70–1.9 (m, 4H). $^{13}$C NMR(DMSO) 167.4, 162.3, 159.9, 159.3, 157.5, 156.9, 142.3, 142.3, 134.1, 134.0, 128.0, 127.7, 127.6, 118.4, 118.3, 116.0, 115.8, 114.9, 114.7, 71.2, 59.7, 59.5, 36.5, 24.6.

EXAMPLE 6

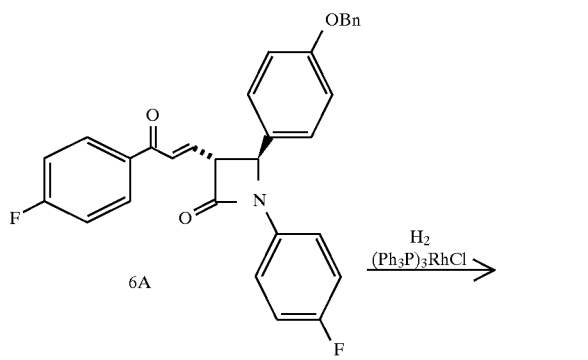

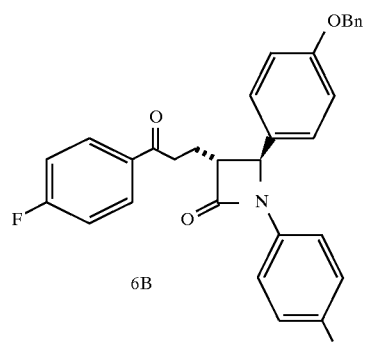

The crude compound 6A, generated from dehydration step from 80 mmol of aldol condensation product, was dissolved in 120 ml of CH$_2$Cl$_2$ to which 2.2g (2.4 mmol) of the catalyst was added. The mixture was subjected hydrogenation at 60 psi for 18 hr. Concentration of the reaction gave a residue of the product, which was separated by column with hexane and EtOAc (90:10) to give 27.5 g pure product, 71% from aldol condensation product as starting material. $^1$H NMR (CDCl$_3$) 7.98 (dd, J=8.5, 5.5 Hz, 1H), 7.41 (m, 5H), 7.25 (m, 4H), 7.12 (t, J=8.5, 2H), 6.55 (m, 4H), 5.04 (s, 2H), 4.68 (d, J=2.1, 1H), 3.65 (m, 1H), 3.28 (m, 1H), 3.16 (m, 1H), 2.40 (m, 1H), 2.28 (m, 1H).

EXAMPLE 7

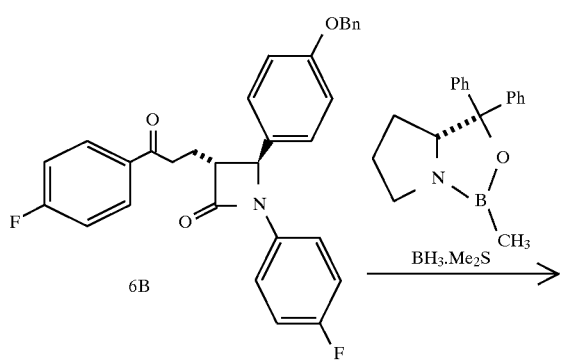

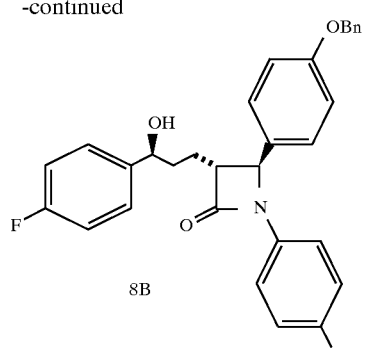

To a 250 mL oven-dried flask with a magnetic stirrer were added 6.2 g (12.5 mmol) of compound 6B and 60 mL of CH$_2$Cl$_2$. To the resulting solution at −20° C. were added sequentially 0.1 equivalent of the chiral catalyst and 6.3 mL (12.5 mmol) of 2.0N BH$_3$.(CH$_3$)$_2$S over 2 h. The reaction was allowed to warm to 0° C., it was stirred at that temperature for 1 h and quenched with CH$_3$OH. The quenched solution was concentrated and extracted with CH$_2$Cl$_2$. The organic layer was concentrated and the residue was recrystallized from EtOAc and hexanes to give 4.1 g (70%) of 8B. The e.e. was determined by HPLC and found to be 93%. $^1$H NMR (CDCl$_3$): 6 7.45–7.15 (m, 11H), 7.00–6.80 (m, 6H), 4.98 (s, 2H), 4.70–4.60 (m, 1H), 4.50 (d, 1H), 3.05–2.97 (m, 1H), 2.20–2.10 (m, 1H), 1.95–1.75 (m, 4H).

EXAMPLE 8

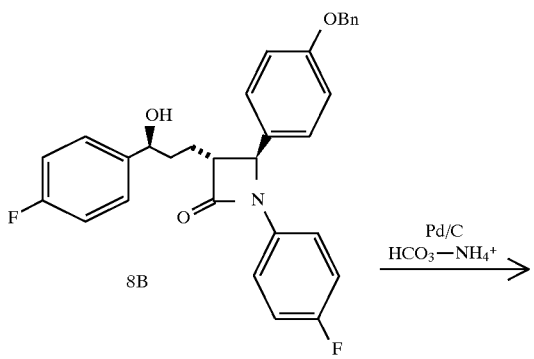

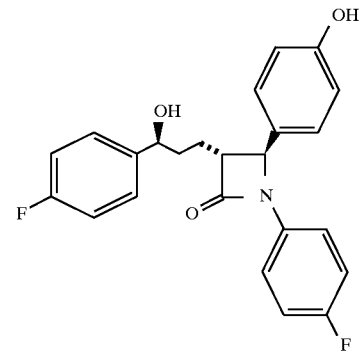

To a flask were added Pd-C (10%) (1 g, 5% by w/w), ammonium bicarbonate (11.4 g, 181 mmole), compound 8B (18.1 g, 36.3 mmole) and CH$_3$OH (250 mL) carefully at r.t. under N$_2$. HOAc was added to adjust the pH to 3–5 and the resultant mixture was heated at 45° to 55° C. until the reaction finished as determined by TLC (about 2–3hr). During the reaction, the pH was controlled in the range of 3–5 by adding HOAc. The reaction was filtered and the solvent evaporated. The residue was dissolved in t-BuOMe and washed with water. After drying over $Na_2SO_4$ and evaporating the solvent, the product was purified by recrystallization in t-BuOMe/heptane and $CH_3OH$/water to give 11.75 g (79%). $^1H$ NMR (DMSO): 9.54 (s, 1H), 7.32 (dd, J=8.3, 5.7 Hz, 2H), 7.21 (m, 4H), 7.35 (m, 4H), 6.77 (d, J=8.3 Hz, 2H), 5.3 (d, J=4.6 Hz, 1H), 4.82 (d, J=2.1 Hz, 1H), 4.50 (m, 1H), 3.10 (m, 1H), 1,70–1.9 (m, 4H). $^{13}C$ NMR (DMSO) 167.4, 162.3, 159.9, 159.3, 157.5, 156.9, 142.3, 142.3, 134.1, 134.0, 128.0, 127.7, 127.6, 118.4, 118.3, 116.0, 115.8, 114.9, 114.7, 71.2, 59.7, 59.5, 36.5, 24.6.

EXAMPLE 9

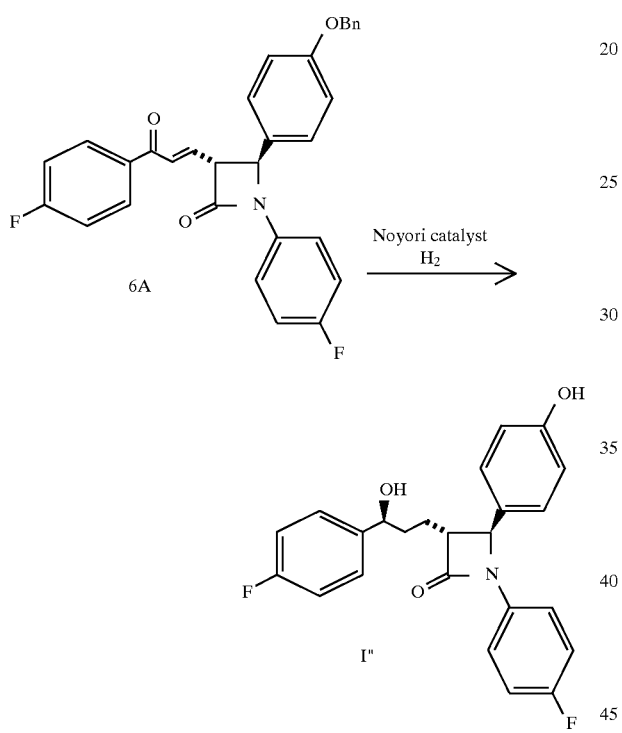

(Cyclooctadienyl)ruthenium dichloride (107 mg, 0.38 mmol) and (R)-2,2'-bis)diphenylphosphino)-1,1'-binaphthyl (BINAP) (250 mg, 0.40 mmol) were placed in a flask and connected to Schlenck apparatus with another flask at the opposite end. The entire apparatus was evacuated, then filled with $N_2$. Toluene (10 mL) and $Et_3N$ (1 mL), after deoxygenation several times, was charged into the lower flask, which was then heated to 140°–145° C. for 4 h. After cooling to r.t., red solid precipitated out of solution. The solid was filtered and washed with degased toluene inside of the apparatus under $N_2$. The entire apparatus was evacuated and the solid was dried.

Compound 6A (50 mg, 0.1 mmol), the catalyst, [(R)—Ru(BINAP)$Cl_2$]$_2$.$NEt_3$, prepared above (<10 mg, <0.01 mmol) and $CH_3OH$ (50 mL) with 1 drop of 2N HCl were charged in an autoclave under $N_2$. The reaction was subjected to 850 psi $H_2$ at 80° C. for 48 h. Major product (I") was found and matched in TLC and HPLC profile with the product of Example 5.

EXAMPLE 10

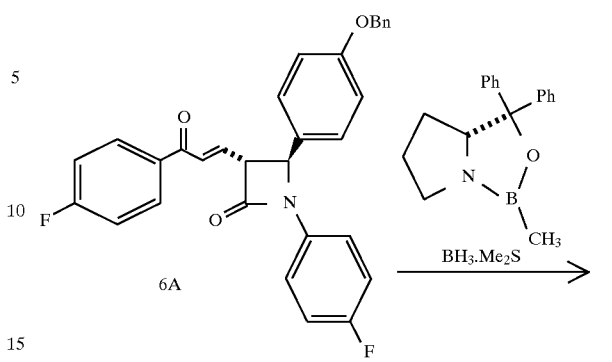

To a mixture of 300 mg (0.61 mmol) of 6A and 0.1 equivalent of the chiral catalyst in 5 mL of $CH_2Cl_2$ at −15° C., 0.21 mL (0.4 mmol) of 2.0N $BH_3.(CH_3)_2S$ was added dropwise over 5 min. The reaction was allowed to warm to 0° C., it was stirred for 45 min. and quenched with $CH_3OH$. Concentration, followed by chromatography gave compound XI. The e.e. was determined to be 75%. $^1H$ NMR (CDCl$_3$): δ7.55–6.82 (m, 18H), 5.95 (d, 1H), 5.15 (d, 1H), 4.98 (s, 2H), 4.65 (d, 1H), 3.65 (d, 1H).

We claim:
1. A process for producing a compound of the formula wherein:
$R_1$, $R_2$ and $R_3$ are independently selected from the group consisting of:
(a) H;
(b) halo;
(c) —O$R_5$, wherein: $R_5$ is selected from the group consisting of H, $C_1$ to $C_6$ alkyl, aryl, aralkyl, heteroaryl, and $C_3$ to $C_7$ cycloalkyl; and
(d) —C(O)$R_8$, wherein: $R_8$ is selected from the group consisting of —O$R_9$ and —N($R_{10}$)$_2$; $R_9$ is selected from the group consisting of $C_1$ to $C_6$ alkyl and aryl; and each $R_{10}$ is independently selected from the group consisting of H, $C_1$ to $C_6$ alkyl and aryl;

comprising (a) reacting lactone of formula II

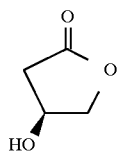

with an imine of formula III

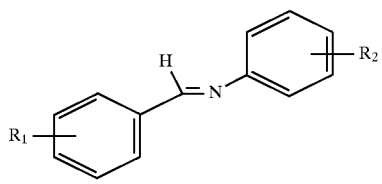

in the presence of a base and optionally in the presence of a cyclization promoter selected from the group consisting of LiCl and LiBr to obtain a chiral diol of formula IV

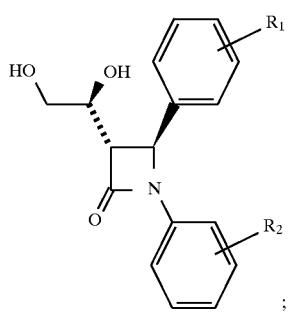

(b) oxidizing the chiral diol of formula IV to the corresponding aldehyde of formula V

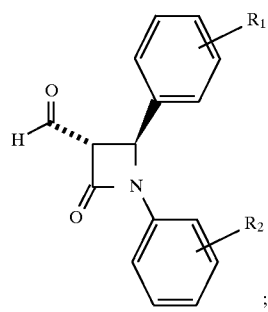

(c) condensing the aldehyde of formula V with a compound of the formula E

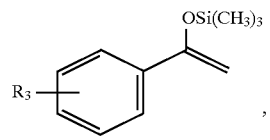

followed by dehydration to obtain a compound of formula VI

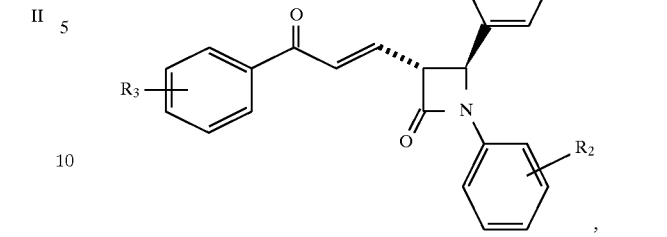

(d) hydrogenating a compound of formula VI to form a compound of formula VII

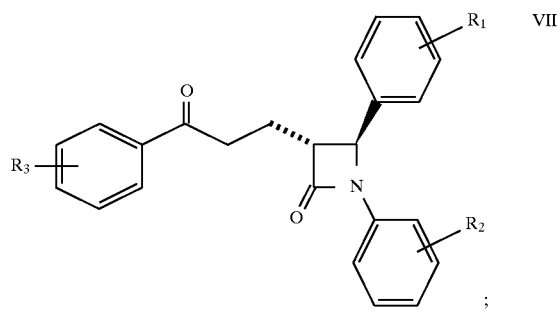

(e) conducting a chiral catalytic reduction of the compound of formula VII with a chiral catalyst to obtain a compound of formula I;

(f) optionally, when any of $R_1$, $R_2$ or $R_3$ is a benzyloxy or alkoxy group, converting said benzyloxy or alkoxy group to a hydroxy group to obtain a compound of formula I.

2. A process according to claim 1, wherein step (a) is carried out using Na—LiHMDA as the base.

3. A process according to claim 1, wherein step (a) is carried out at about $-30°$ to about $-40°$ C.

4. A process according to claim 1, wherein step (a) is carried out using LiCl as a cyclization promotor.

5. A process according to claim 1, wherein step (b) is carried out using $NaIO_4$ as the oxidizing agent.

6. A process according to claim 1, wherein the chiral reduction catalyst used in step (e) is

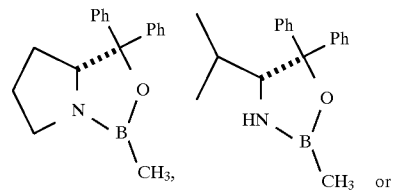 or

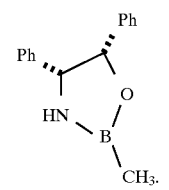

7. A process according to claim 1, which further comprises removing cis β-lactam by crystallization before carrying out step (f).

8. A process according to claim 1 for producing the compound of the formula

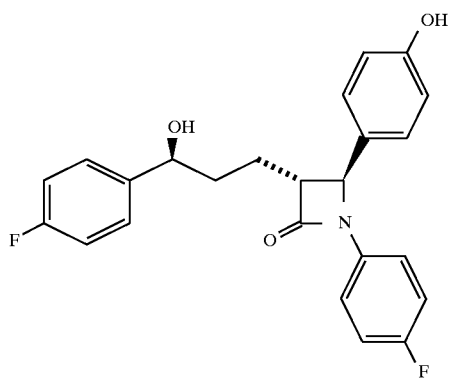

comprising (a) reacting lactone of formula II

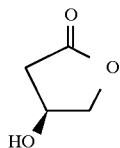

II with an imine of formula III'

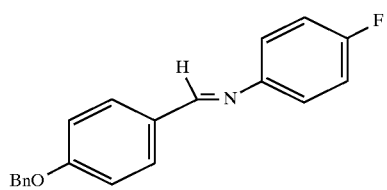

III' wherein Bn is benzyl, in the presence of a base and optionally in the presence of a cyclization promoter selected from the group consisting of LiCl and LiBr to obtain a chiral diol of formula IV'

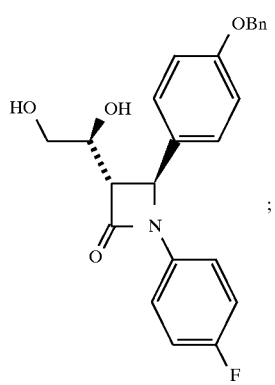

IV'

(b) oxidizing the chiral diol of formula IV' to the corresponding aldehyde of formula V'

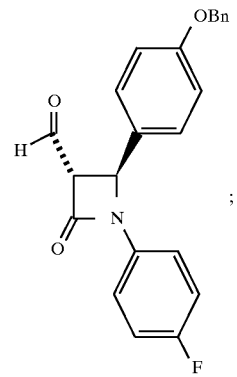

V'

(c) condensing the aldehyde of formula V' with a compound of the formula E'

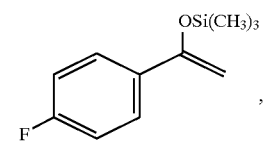

followed by dehydration to obtain a compound of formula VI'

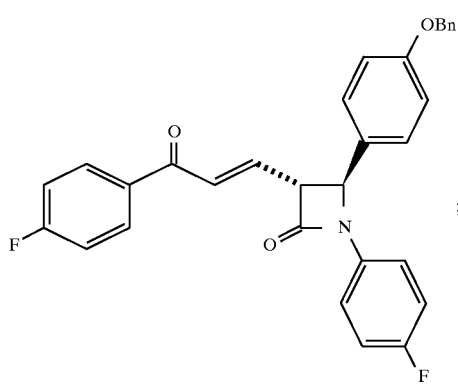

VI'

(d) hydrogenating a compound of formula VI' to form a compound of formula VII'

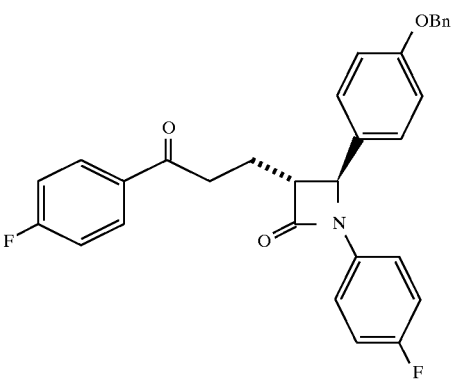

VII'

(e) conducting a chiral catalytic reduction of the compound of formula VII' with a chiral catalyst of the formula

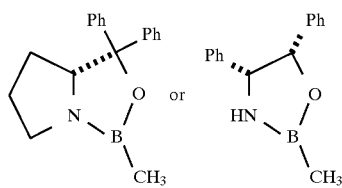

to obtain a compound of formula I'

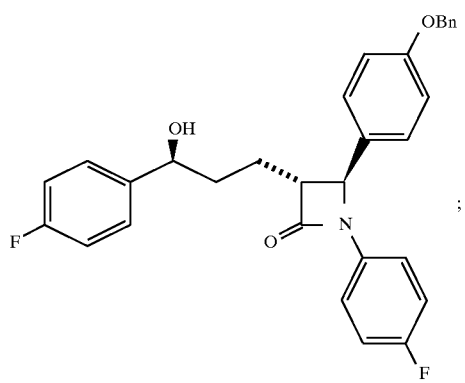

and (f) debenzylating the compound of formula I'.

9. A process for preparing a compound of the formula XI

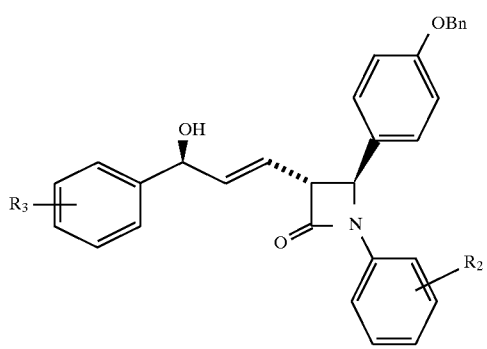

wherein Bn is benzyl; and $R_2$ and $R_3$ are independently selected from the group consisting of:

(a) H;

(b) halo;

(c) —$OR_5$, wherein: $R_5$ is selected from the group consisting of H, $C_1$ to $C_6$ alkyl, aryl, aralkyl, heteroaryl, and $C_3$ to $C_7$ cycloalkyl; and (d) —$C(O)R_8$, wherein: $R_8$ is selected from the group consisting of —$OR_9$ and —$N(R_{10})2$; $R_9$ is selected from the group consisting of $C_1$ to $C_6$ alkyl and aryl; and each $R_{10}$ is independently selected from the group consisting of H, $C_1$ to $C_6$ alkyl and aryl;

comprising chirally reducing the compound of formula VI"

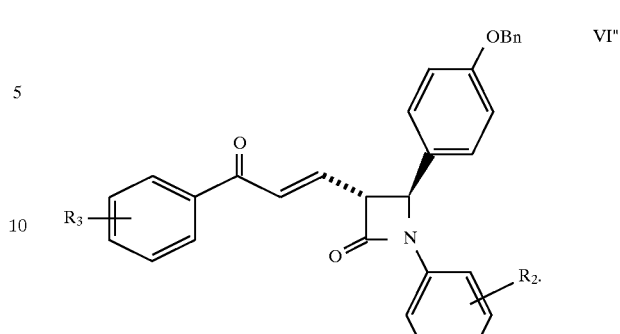

10. A process for preparing a compound of formula VI

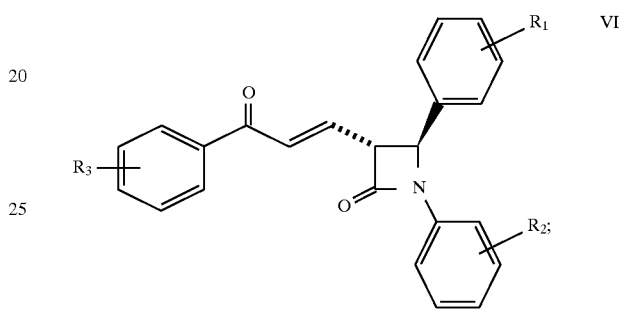

wherein $R_1$, $R_2$ and $R_3$ are independently selected from the group consisting of:

(a) H;

(b) halo;

(c) —$OR_5$, wherein: $R_5$ is selected from the group consisting of H, $C_1$ to $C_6$ alkyl, aryl, aralkyl, heteroaryl, and $C_3$ to $C_7$ cycloalkyl; and (d) —$C(O)R_8$, wherein: $R_8$ is selected from the group consisting of —$OR_9$ and —$N(R_{10})_2$; $R_9$ is selected from the group consisting of $C_1$ to $C_6$ alkyl and aryl; and each $R_{10}$ is independently selected from the group consisting of H, $C_1$ to $C_6$ alkyl and aryl;

comprising condensing an aldehyde of formula V

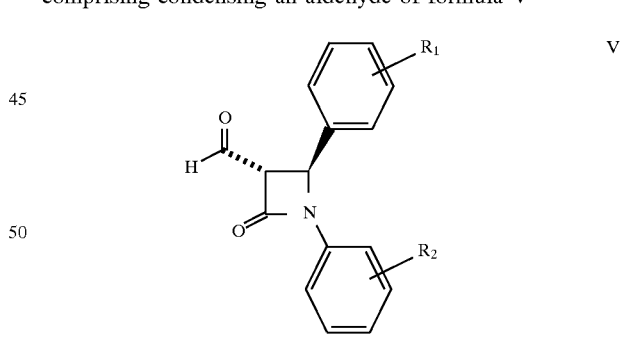

wherein $R_1$ and $R_2$ are as defined above, with a compound of the formula E

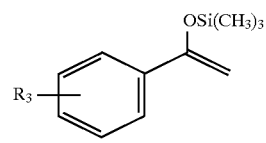

wherein R₃ is as defined above, followed by dehydration.

11. A process for preparing a compound of the formula VII

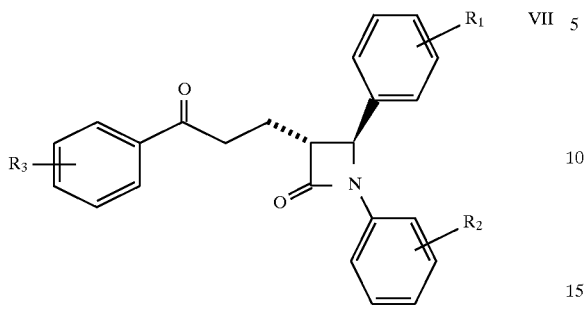

wherein R₁, R₂ and R₃ are independently selected from the group consisting of:
(a) H;
(b) halo;
(c) —OR₅, wherein: R₅ is selected from the group consisting of H, C₁ to C₆ alkyl, aryl, aralkyl, heteroaryl, and C₃ to C₇ cycloalkyl; and
(d) —C(O)R₈, wherein: R₈ is selected from the group consisting of —OR₉ and —N(R₁₀)₂; R₉ is selected from the group consisting of C₁ to C₆ alkyl and aryl; and each R₁₀ is independently selected from the group consisting of H, C₁ to C₆ alkyl and aryl;
comprising hydrogenating a compound of formula VI

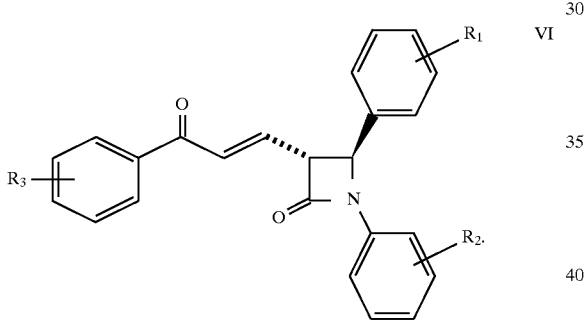

12. A process for preparing a compound of the formula X

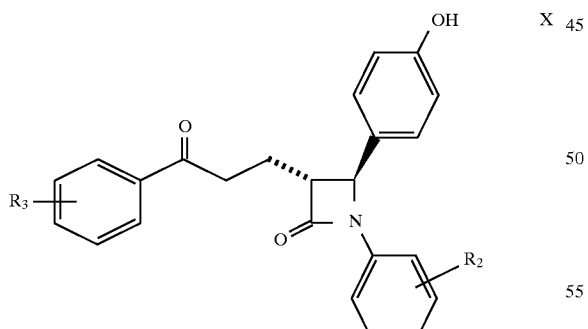

wherein R₂ and R₃ are independently selected from the group consisting of:
(a) H;
(b) halo;
(c) —OR₅, wherein: R₅ is selected from the group consisting of H, C₁ to C₆ alkyl, aryl, aralkyl, heteroaryl, and C₃ to C₇ cycloalkyl; and
(d) —C(O)R₈, wherein: R₈ is selected from the group consisting of —OR₉ and —N(R₁₀)₂; R₉ is selected from the group consisting of C₁ to C₆ alkyl and aryl; and each R₁₀ is independently selected from the group consisting of H, C₁ to C₆ alkyl and aryl;

comprising hydrogenating a compound of the formula VI″

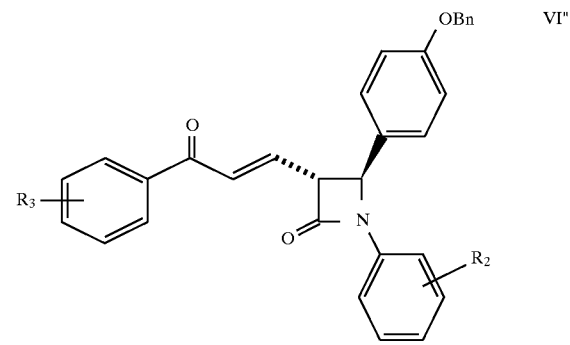

wherein Bn is benzyl.

13. A process for preparing a compound of the formula V

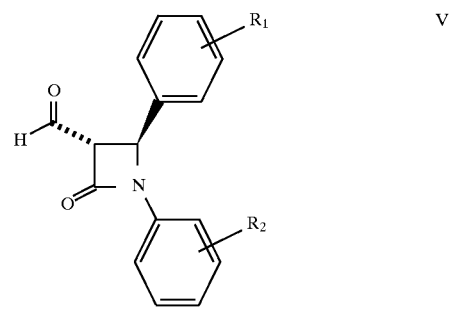

wherein R₁ and R₂ are independently selected from the group consisting of:
(a) H;
(b) halo;
(c) —OR₅, wherein: R₅ is selected from the group consisting of H, C₁ to C₆ alkyl, aryl, aralkyl, heteroaryl, and C₃ to C₇ cycloalkyl; and
(d) —C(O)R₈, wherein: R₈ is selected from the group consisting of —OR₉ and -N(R₁₀)₂; R₉ is selected from the group consisting of C₁ to C₆ alkyl and aryl; and each R₁₀ is independently selected from the group consisting of H, C₁ to C₆ alkyl and aryl;

comprising oxidizing a chiral diol of formula IV

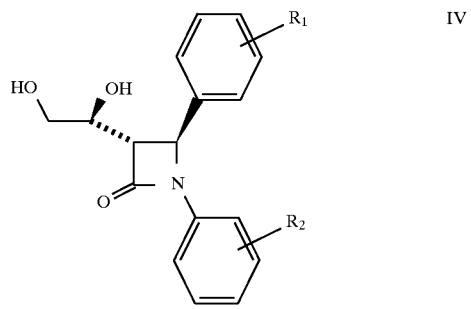

wherein R₁ and R₂ are as defined above.

* * * * *